(12) United States Patent
Yokobayashi et al.

(10) Patent No.: US 8,379,209 B2
(45) Date of Patent: Feb. 19, 2013

(54) NON-DESTRUCTIVE INSPECTION DEVICE FOR OXYGEN CONCENTRATION IN BAG-SHAPED CONTAINER

(75) Inventors: Takayasu Yokobayashi, Osaka (JP); Kazuaki Sasaki, Osaka (JP); Tohru Hosokawa, Osaka (JP)

(73) Assignee: Hitachi Zosen Corporation, Osaka (JP)

( * ) Notice: Subject to any disclaimer, the term of this patent is extended or adjusted under 35 U.S.C. 154(b) by 91 days.

(21) Appl. No.: 13/057,496

(22) PCT Filed: Jun. 24, 2009

(86) PCT No.: PCT/JP2009/002881
§ 371 (c)(1),
(2), (4) Date: Feb. 4, 2011

(87) PCT Pub. No.: WO2010/016184
PCT Pub. Date: Feb. 11, 2010

(65) Prior Publication Data
US 2011/0134431 A1    Jun. 9, 2011

(30) Foreign Application Priority Data
Aug. 8, 2008 (JP) ................................. 2008-204910

(51) Int. Cl.
  G01N 21/00    (2006.01)
(52) U.S. Cl. ....................................................... 356/437
(58) Field of Classification Search .................. None
See application file for complete search history.

(56) References Cited

U.S. PATENT DOCUMENTS

| 5,173,749 | A | 12/1992 | Tell et al. | 356/437 |
| 7,414,727 | B2 * | 8/2008 | Willing et al. | 356/437 |
| 7,456,969 | B2 * | 11/2008 | Chabanis et al. | 356/437 |
| 7,586,613 | B2 * | 9/2009 | Wilkins et al. | 356/437 |
| 2005/0084974 | A1 | 4/2005 | Veale et al. | 436/43 |

FOREIGN PATENT DOCUMENTS

| JP | 3-505782 | 12/1991 |
| JP | 08-184554 | 7/1996 |
| JP | 2004-067224 | 3/2004 |
| JP | 3742042 | 2/2006 |
| JP | 2006-250836 | 9/2006 |
| JP | 2007-508567 | 4/2007 |
| JP | 2009-014589 | 1/2009 |

OTHER PUBLICATIONS

International Search Report for International Application No. PCT/JP2009/002881, Oct. 6, 2009.

* cited by examiner

*Primary Examiner* — Tu Nguyen
(74) *Attorney, Agent, or Firm* — Kusner & Jaffe (57) ABSTRACT

A non-destructive inspection device for an oxygen concentration in a bag-shaped container includes: right and left affixing plates provided so as to be moved toward and away from the bag-shaped container; a laser emitting section for measuring an oxygen concentration that is provided on one of the affixing plates; and a laser receiving section on the other affixing plate, wherein the end faces of the emitting section and the receiving section have gas-filled chambers that include gas chambers with a constant length and are made of a translucent material. In the measurement of an oxygen concentration, the affixing plates are brought close to each other, the thickness of a gas phase portion is kept constant, and air is removed between the end faces of the emitting section and the receiving section and the surfaces of the container.

4 Claims, 9 Drawing Sheets

NON-DESTRUCTIVE INSPECTION DEVICE FOR OXYGEN CONCENTRATION IN BAG-SHAPED CONTAINER

FIELD OF THE INVENTION

The present invention relates to a non-destructive inspection device provided in a liquid filler to inspect an oxygen concentration in a bag-shaped container filled with a liquid.

BACKGROUND OF THE INVENTION

Medical infusions are injected into bag-shaped containers, e.g., infusion bags and then are transported and stored.

Such a bag filled with a medical infusion contains nitrogen gas to prevent the oxidation and degradation of the infusion. After a bag is filled with an infusion, the oxygen concentration of the infusion is measured to inspect whether the infusion is defective or not. In other words, it is naturally preferable that less oxygen is entrained during manufacture, and thus when the oxygen concentration is higher than a permissible value, it is decided that the product is defective.

This inspection is conducted by a destructive method in which an injection needle is inserted into a product bag serving as a sample and air is collected to measure the oxygen concentration. After the inspection, the sample is discarded. Since the inspection is not a one hundred percent inspection but a sample inspection, safety and sanitation may not be secured.

For products in vial containers other than products in infusion bags, a method is available in which oxygen entrained or present in a container in the manufacturing process is detected by a laser beam (e.g., see National Publication of International Patent Application No. 2007-508567).

Specifically, in this method, a laser beam is transmitted to a gas phase portion on the top of a vial container and the amount of transmitted light is measured. In other words, the absorbance is detected to measure an oxygen concentration.

SUMMARY OF INVENTION

Technical Problem

When an oxygen concentration in a bag is measured by a laser beam, it is necessary to keep constant the transmission distance of the laser beam because different transmission distances naturally cause variations in measured oxygen concentrations.

As described in National Publication of International Patent Application No. 2007-508567, a vial container is hard and thus a laser beam is transmitted at a constant distance, so that an oxygen concentration can be measured with relatively high accuracy.

However, infusion bags are made of soft materials and vary in thickness, so that non-destructive inspections using laser beams cannot be conducted with high accuracy.

An object of the present invention is to provide a non-destructive inspection device which can accurately inspect an oxygen concentration in a bag-shaped container filled with a liquid, by a laser beam in a non-destructive inspection.

Solution to Problem

In order to solve the problem, a non-destructive inspection device for an oxygen concentration in a bag-shaped container according to a first aspect of the present invention is a non-destructive inspection device provided in a liquid filler for feeding a liquid into the bag-shaped container held by a container holder on a transport unit and transported along a transport path including at least a liquid filling area, a sealing area, and an inspection area, the non-destructive inspection device emitting, in the inspection area of the transport path, a laser beam to the gas phase portion of the bag-shaped container filled with the liquid and measuring an oxygen concentration in the bag-shaped container based on the amount of transmitted light, the non-destructive inspection device including: a pair of right and left moving members provided on the right and left of the inspection area of the transport path such that the moving members are moved toward and away from the bag-shaped container by a moving device; a laser emitting section that is provided on one of the moving members and emits the laser beam for measuring the oxygen concentration; and a laser receiving section that is provided on the other moving member and receives the laser beam, wherein the non-destructive inspection device further includes inert gas chambers respectively on the end faces of the laser emitting section and the laser receiving section on the moving members, the inert gas chambers being made of a translucent material with a constant length in a depth direction, and in the measurement of the oxygen concentration in the inspection area, the pair of right and left moving members are brought close to each other to contact the end faces of the laser emitting section and the laser receiving section with the surfaces of the gas phase portion of the bag-shaped container, so that the gas phase portion has a constant thickness and air is removed between the end faces of the laser emitting section and the laser receiving section and the surfaces of the gas phase portion.

A non-destructive inspection device for an oxygen concentration in a bag-shaped container according to a second aspect, in the non-destructive inspection device of the first aspect, further includes two calibration containers that are made of a translucent material outside the inspection area and are filled beforehand with inert gas having different oxygen concentrations, wherein the pair of moving members having the laser emitting section and the laser receiving section are movable to calibration positions for measuring the oxygen concentrations in the calibration containers.

A non-destructive inspection device for an oxygen concentration in a bag-shaped container according to a third aspect, in the non-destructive inspection device of the first aspect, wherein in the inspections of the bag-shaped containers, the transport unit is stopped, and the pair of moving members having the laser emitting section and the laser receiving section is movable to the stopped bag-shaped containers.

A non-destructive inspection device for an oxygen concentration in a bag-shaped container according to a fourth aspect, in the non-destructive inspection device of the first aspect, wherein the transport path of the containers is circular or oval.

Advantageous Effects of Invention

According to this configuration, inert gas chambers on the ends of a laser emitting section and a laser receiving section are filled with nitrogen gas. In this state, the gas phase portion of a container is pressed from both sides to a constant thickness by the end faces of the laser emitting section and the laser receiving section, air is removed between the end faces of the laser emitting section and the laser receiving section and the surface of the gas phase portion of the bag-shaped container, and a laser beam is emitted to measure an oxygen concentration. Thus even when the container is a soft bag, it is possible to accurately measure the oxygen concentration and determine the quality of a product (in other words, whether the oxygen concentration is proper or not). In order to accurately measure an oxygen concentration in a soft container such as a bag, it is necessary to collect gas in the bag and thus only a sample inspection can be conducted, whereas the foregoing configuration can achieve a one hundred percent inspection.

DETAILED DESCRIPTION OF THE INVENTION

Referring to the accompanying drawings, the following will describe a non-destructive inspection device for an oxygen concentration in a bag-shaped container according to an embodiment of the present invention.

The non-destructive inspection device is provided in a liquid filler for filling an infusion bag (an example of a bag-shaped container, hereinafter will be called a container), which is made of a soft material (e.g., a soft plastic such as polyolefin), with a medical infusion such as a drip (hereinafter, will be called a liquid). The non-destructive inspection device inspects whether an oxygen concentration is proper or not in a container that is filled with a liquid and has a sealed inlet. Whether an oxygen concentration is proper or not is decided based on the measured value of the oxygen concentration in the container, the oxygen concentration being measured by a laser beam (this measuring method is called, e.g., tunable semiconductor laser absorption spectroscopy).

First, the configuration of the liquid filler will be simply described below.

As shown in FIGS. 1 to 4, containers 1 serving as infusion bags are sequentially held and transported along a circular transport path 5; meanwhile, a liquid serving as a medical infusion is injected into the empty containers 1, inlets 2 of the containers 1 are sealed, it is inspected whether oxygen concentrations in the infusion bags filled with the liquid are proper or not, protective films are applied to the inlets 2, and then the containers 1 are transported to the subsequent process.

Figure 1:
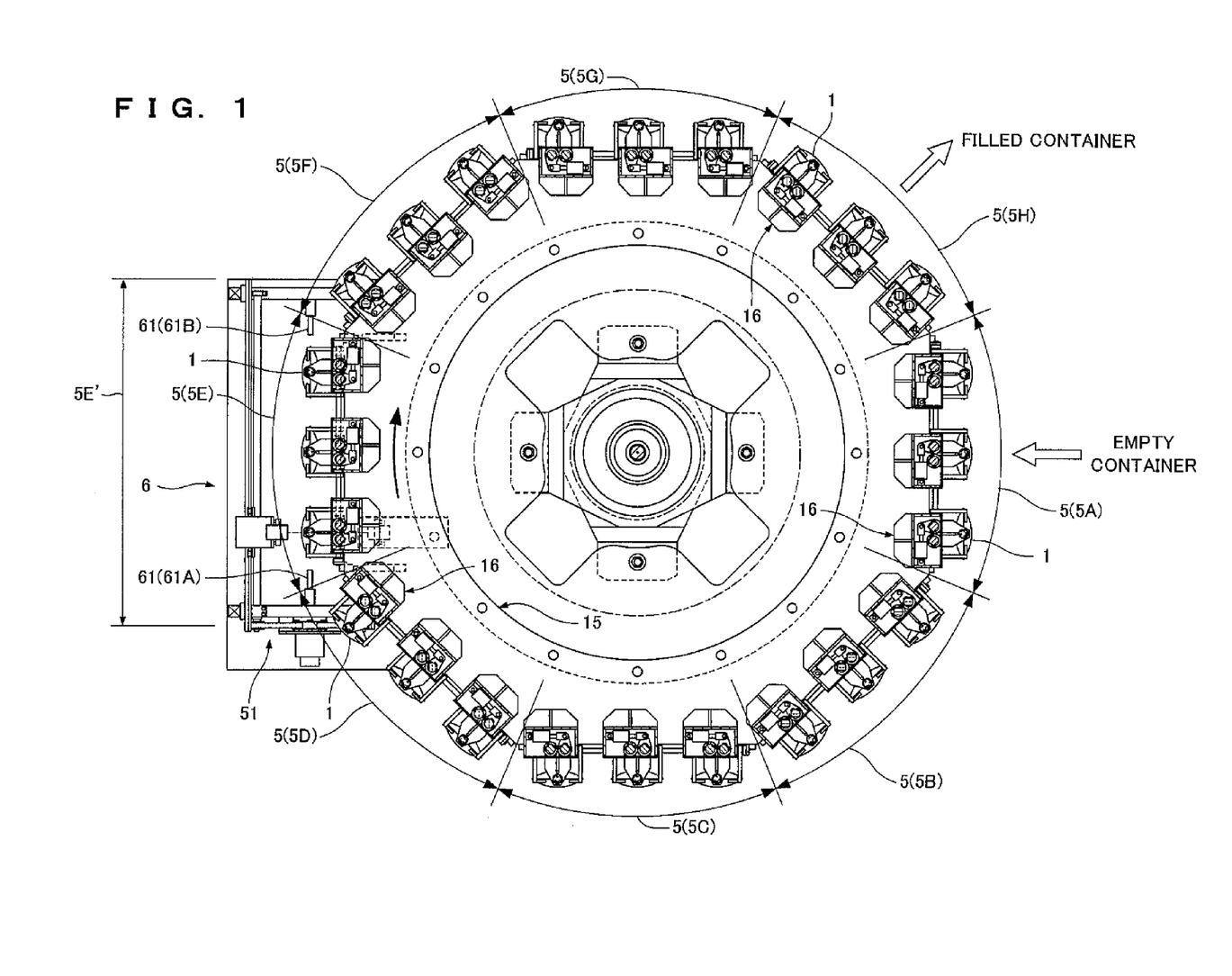
FIG. 1 is a plan view schematically showing the configuration of a liquid filler including a non-destructive inspection device according to an embodiment of the present invention.
Figure 2A:
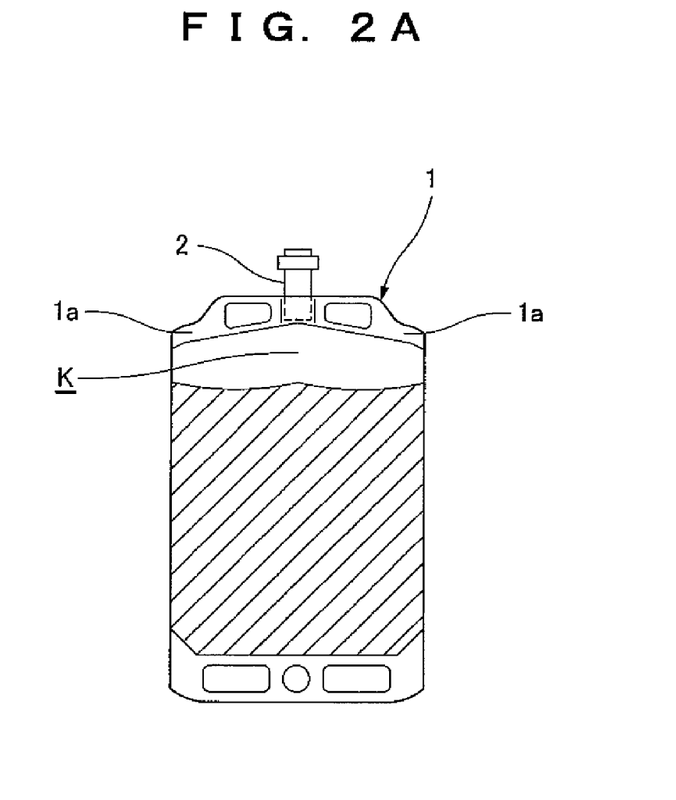
FIG. 2(a) is a front view showing the appearance of a bag-shaped container to be inspected by the non-destructive inspection device.
Figure 2B:
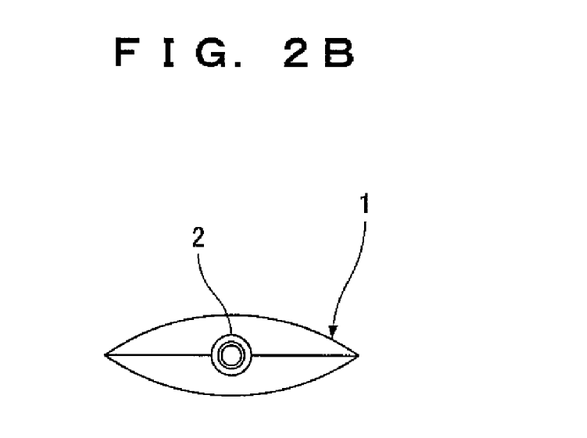
FIG. 2(b) is a plan view showing the appearance of the bag-shaped container.

The transport path 5 includes: a receiving area 5A (hereinafter, the area will be also called a station) for receiving the containers 1; a gas feeding area 5B for feeding inert gas such as nitrogen gas from the inlets 2 into the containers 1; a liquid feeding area 5C for feeding a liquid from the inlets 2 into the containers 1; a sealing area 5D for capping the inlets 2 of the containers 1 filled with the liquid; an inspection area 5E for inspecting gas phase portions K in the capped containers 1; a film attachment area 5F for attaching protective films to the inlets 2; a defective item ejection area 5G for ejecting a defective item; and a delivery area 5H for delivering the containers 1 to the subsequent process. At positions opposed to the receiving area 5A and the delivery area 5H for the containers 1, container feeding/ejecting machines (not shown) are provided that can feed and eject the containers. In the present embodiment, three of the containers 1 are intermittently moved each time and are collectively subjected to operations such as the injection of a liquid.

The liquid filler holds the containers 1 at predetermined intervals and transports the containers 1 along the circular transport path 5. The liquid filler includes: a rotating unit 12 disposed on a pedestal 11; a rotating plate 14 that is connected to a rotating drive shaft 13 disposed perpendicularly to the rotating unit 12 and can be rotated in the horizontal plane; a ring plate (including an inner plate and an outer plate) 15 connected to the outer periphery of the rotating plate 14; and container holders 16 that are disposed at predetermined intervals on the ring plate 15 to hold the containers 1. Further, the rotating unit 12 intermittently rotates the rotating plate 14, that is, the ring plate 15. The rotating unit 12, the rotating drive shaft 13, the rotating plate 14, and the ring plate 15 constitute a transport unit.

Figure 4:
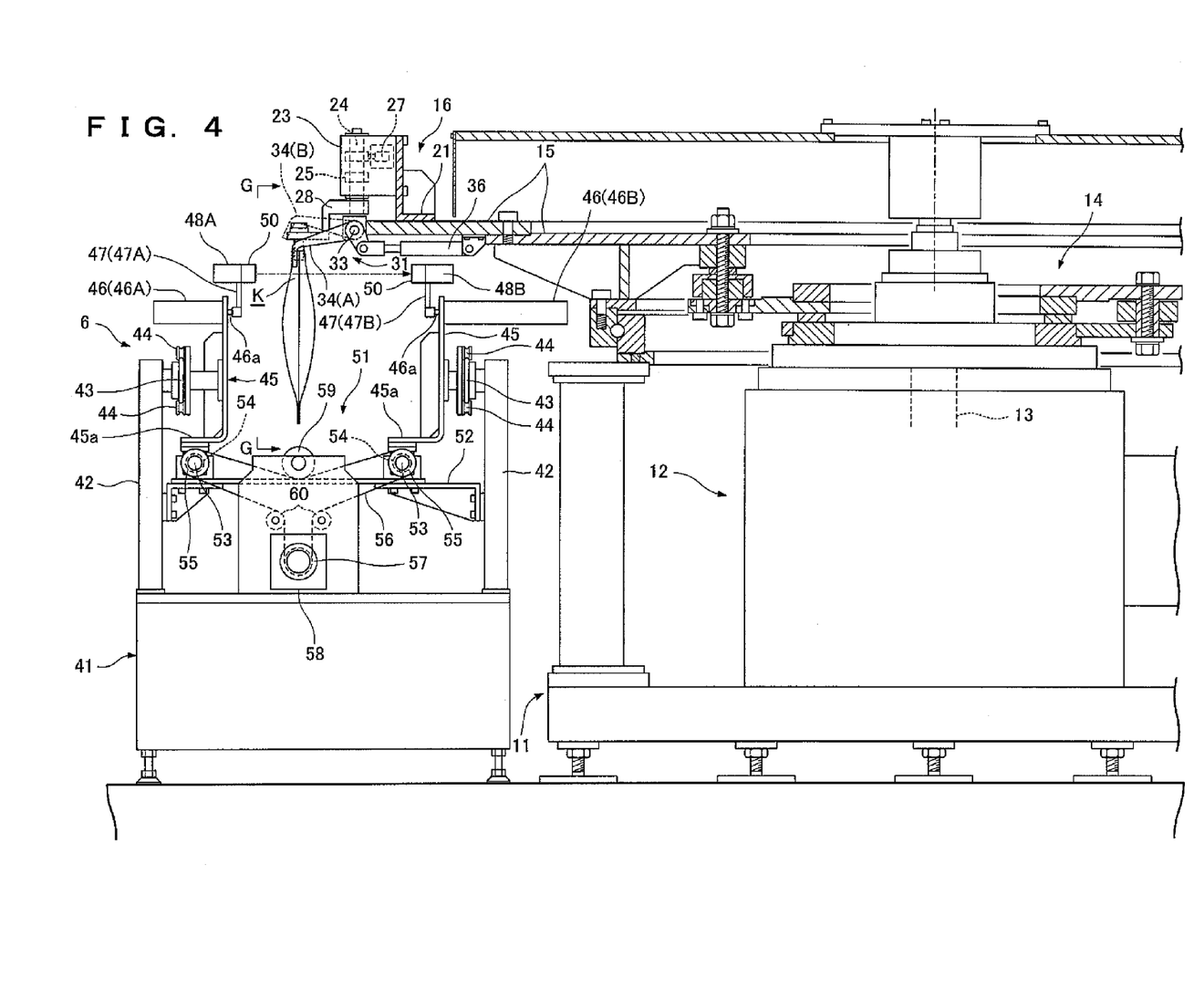
FIG. 4 is an F-F sectional view of FIG. 3.

The container holder 16 includes: an affixing plate 21 fixed to the ring plate 15; a cylindrical member 23 provided on the affixing plate 21; a pair of rotating shafts 24 (24A, 24B) that are rotationally held in the cylindrical member 23 about the vertical axis; a pair of gears 25 (25A, 25B) that are provided on the respective rotating shafts 24 so as to be engaged with each other; a rotating device such as an opening/closing air cylinder that is connected to one of the rotating shafts 24 (24A) via a connecting arm 26 and oscillates (rotates) the rotating shaft 24A within a predetermined angle range; and a pair of holding arms 28 (28A, 28B) that are respectively attached to the lower ends of the rotating shafts 24 so as to hold and release the inlet 2 of the container 1 from both sides.

In this configuration, the opening/closing air cylinder 27 is operated to rotate the rotating shaft 24A. At this point in time, the rotating shaft 24B is rotated in the opposite direction via the pair of gears 25 with the same amount of rotation. Thus the inlet 2 of the container 1 can be held and released by the pair of holding arms 28 from both sides. The ends of the holding arms 28 naturally have recessed portions shaped like, e.g., semicircles such that the holding arms 28 can be engaged with the inlet 2.

Near the container holder 16, that is, the ring plate 15, a container holder 31 is provided that presses a shoulder portion 1a of the container 1 held by the container holder 16, from the outside to the inside (to be precise, from the outside to the inside of the circular transport path). Thus the container 1 is prevented from vibrating.

Figure 3:
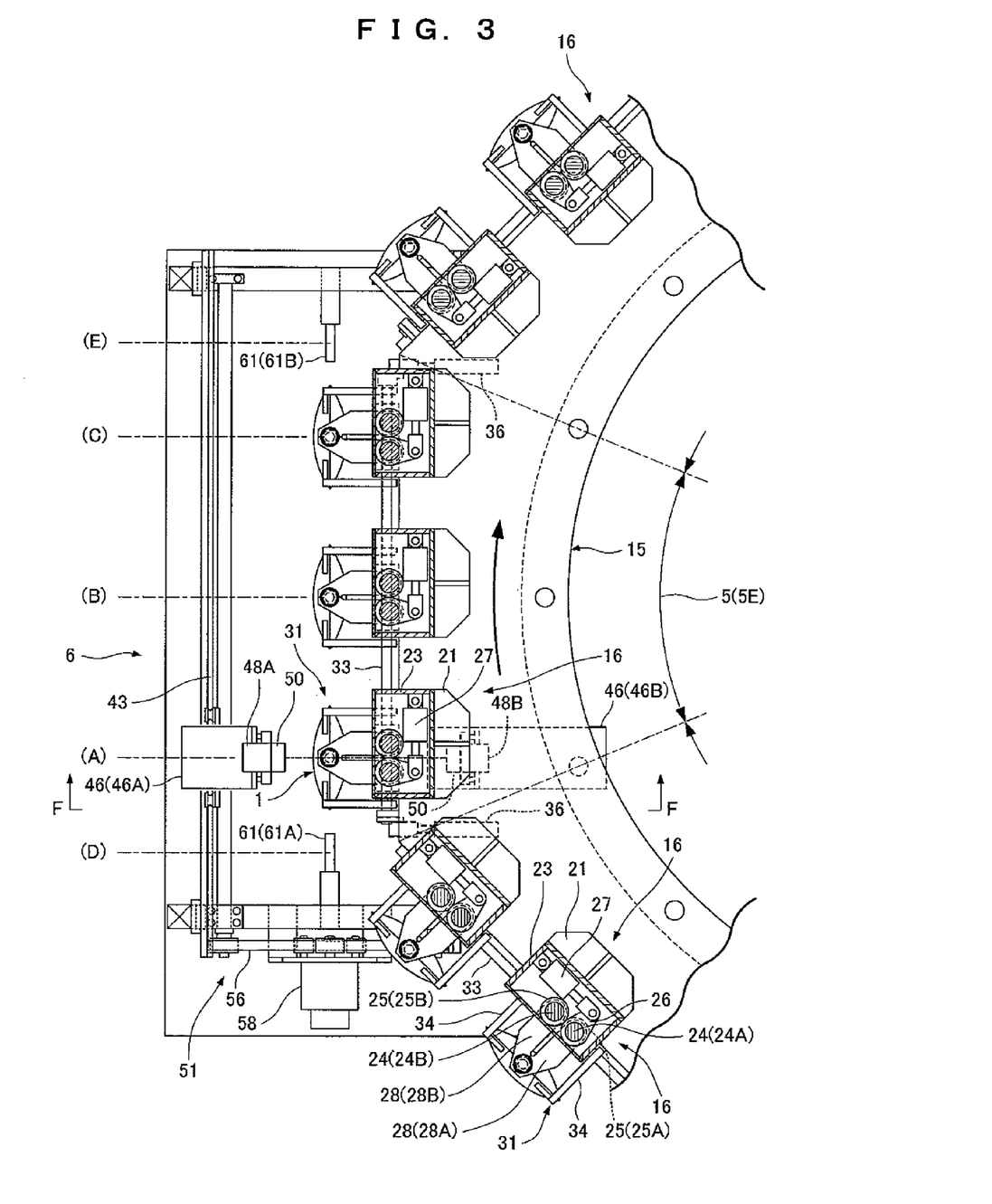
FIG. 3 is a plan view showing the principle part of the non-destructive inspection device.
Figure 5:
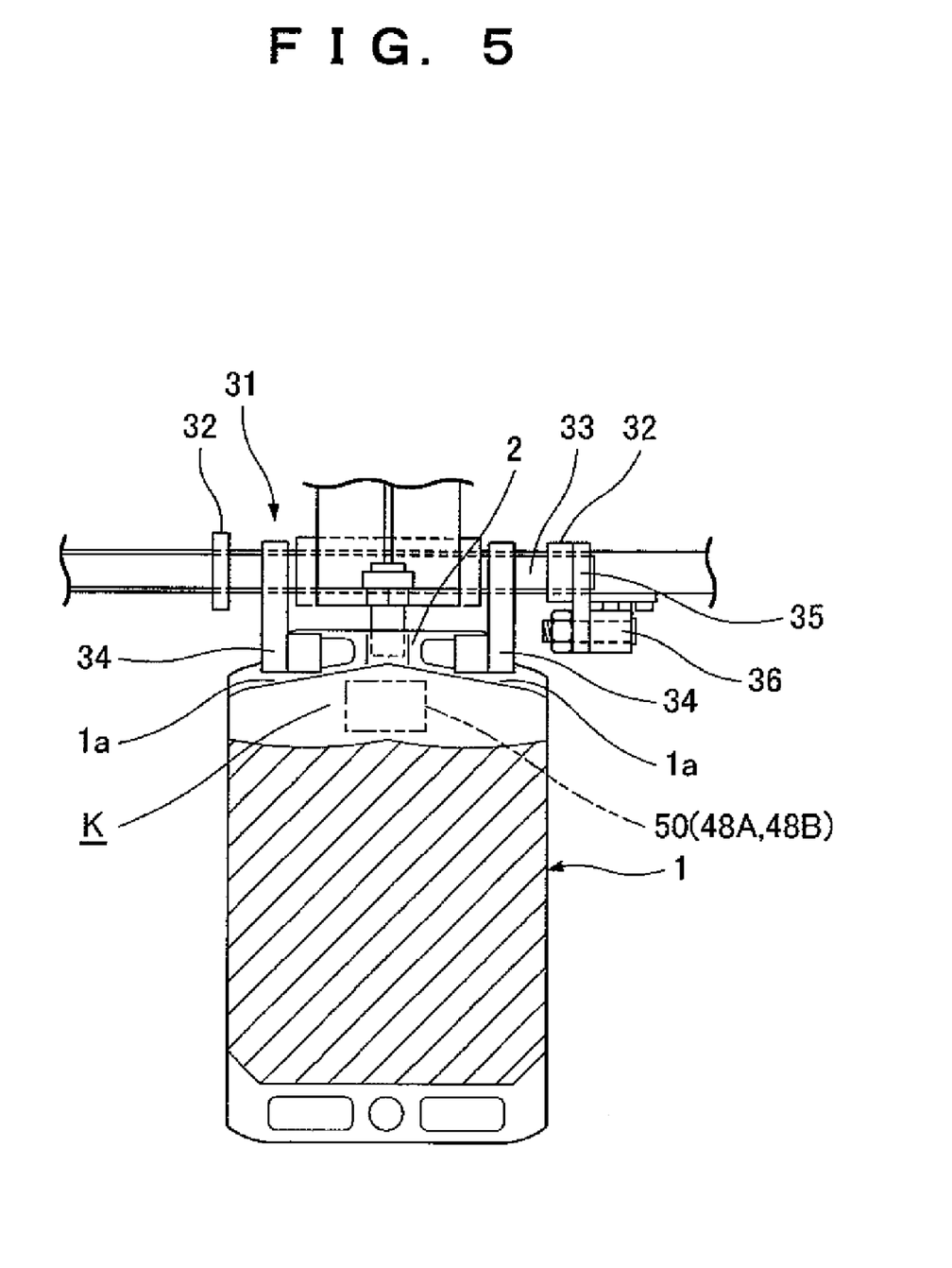
FIG. 5 is a view in the direction of the arrows G-G in FIG. 4.
Figure 6:
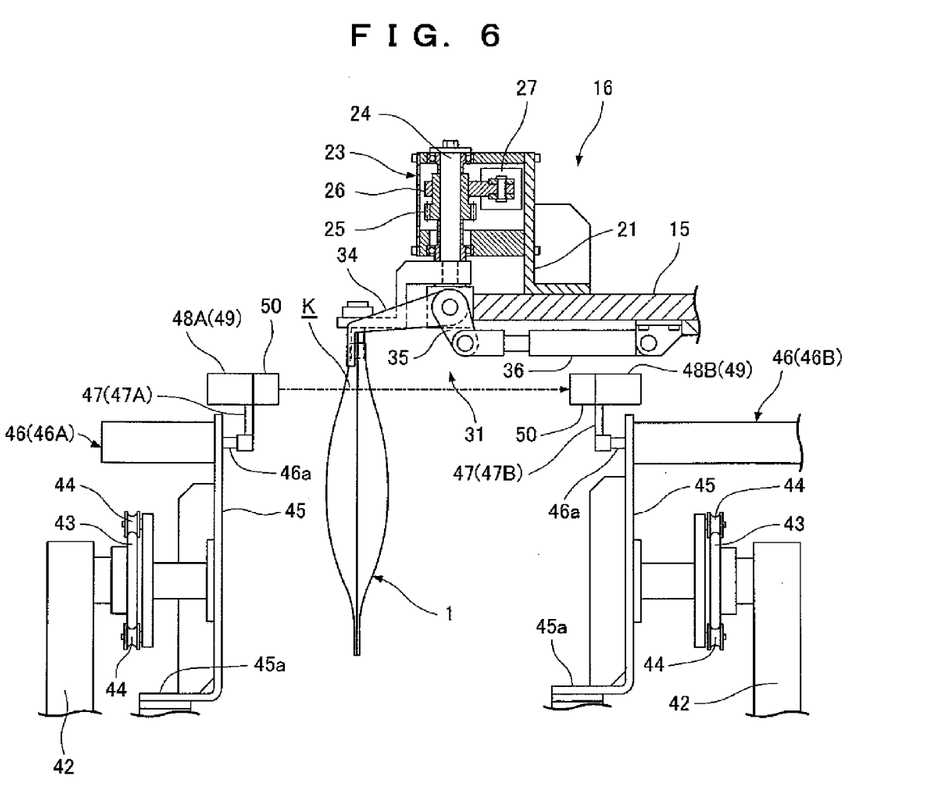
FIG. 6 is a sectional view showing the principle part of the non-destructive inspection device.
Figure 7:
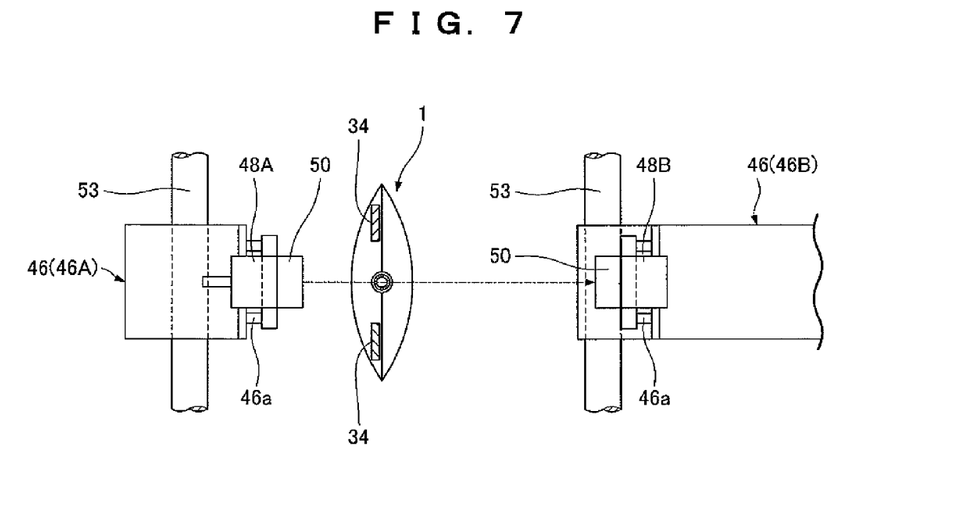
FIG. 7 is a plan view showing the principle part of the non-destructive inspection device.

As shown in FIG. 5, the container holder 31 includes: a rotating shaft 33 attached to the ring plate 15 via a bearing 32 so as to rotate about a horizontal axis parallel with the width direction of the container 1 (that is, the tangential direction of the transport path); a pair of right and left pressing arms 34 fixed, on the rotating shaft 33, at positions on the shoulder portion 1a of the container 1; and an oscillation air cylinder 36 that oscillates the rotating shaft 33 via a connecting lever 35 by a predetermined angle. The rotating shafts 33 are each provided for three of the container holders 16, in other words, the eight rotating shafts 33 are provided in total for the respective areas. The oscillation air cylinders 36 are respectively connected to the ends of the rotating shaft 33. FIG. 3 only shows the pair of oscillation air cylinders 36 that oscillate the rotating shaft 33 located in the inspection area 5E.

In this configuration, the operated oscillation air cylinders 36 rotate the rotating shaft 33 within a predetermined angle range. To be specific, as shown in FIG. 4, the rotating shaft 33 is oscillated between a pressing position (A) where the pressing arms 34 press the surface of the container 1 from the outside to the inside and a release position (B) where the pressing arms 34 are separated from the surface of the container 1.

Further, in the inspection area 5E of the transport path 5, a non-destructive inspection device 6 of the present invention is provided.

During this inspection, the transportation of the containers 1 is stopped and the three containers 1 are sequentially inspected during the single stopping operation. Thus the inspection area 5E is longer than the total length of the three containers 1 held by the container holders 16. Outside the three containers 1, calibration containers (will be described later) are provided for the calibration of the inspection device. The inspection area 5E and the calibration containers constitute an inspection/calibration area 5E'.

Based on the explanation, the non-destructive inspection device will be described below.

As shown in FIGS. 3 to 9, the non-destructive inspection device 6 includes: a support pedestal 41 that is rectangular in plan view in the inspection area 5E having a predetermined length and is provided over the predetermined length at the bottom of the device; a pair of right and left guide members such as guide rails 43 respectively supported by multiple support members 42 raised on the right and left sides of the support pedestal 41; moving plates 45 movably provided on the respective guide rails 43 via guide wheels 44; movement air cylinders (moving devices) 46 (46A, 46B) respectively attached to the upper parts of the moving plates 45; affixing plates (an example of a moving member) 47 (47A, 47B) respectively attached to the ends of rods 46a of the movement air cylinders 46; a laser emitting section 48A attached to the affixing plate 47 to emit an inspection laser beam and a laser receiving section 48B for receiving the inspection laser beam; gas-filled chambers that are respectively provided at the fronts of the laser emitting section 48A and the laser receiving section 48B, are attached to the respective affixing plates 47, are made of a translucent material and have gas chambers (inert gas chambers) filled with nitrogen gas; and a moving apparatus 51 for simultaneously moving the right and left moving plates 45 in the inspection/calibration area 5E'. Of the right and left affixing plates 47, for example, the left affixing plate 47A in FIG. 4 has the laser emitting section 48A and the right affixing plate 47B has the laser receiving section 48B. As a matter of course, the positions of the laser emitting section 48A and the laser receiving section 48B may be switched. The laser emitting section 48A and the laser receiving section 48B may be called inspection tools 49.

The moving apparatus 51 includes: screw shafts (also serving as guide members) 53 for ball screws respectively supported via brackets 52 between the right and left support members 42; nuts (guided members) 54 that are screwed onto the screw shafts 53 via balls and are respectively connected to lower-end bending portions 45a of the moving plates 45; driven-side sprockets 55 respectively attached to the ends of the right and left screw shafts 53; and an electric motor 58 that rotates a driving-side sprocket 57 engaged with a transmission belt wound around the driven-side sprockets 55. At an intermediate point of the transmission belt 56, a sprocket 59 is provided for pressing the transmission belt and sprockets 60 are provided for tensing the transmission belt.

In this configuration, when the electric motor 58 is driven to rotate the screw shafts 53, the right and left moving plates 45, that is, the laser emitting section 48A and the laser receiving section 48B are simultaneously moved to the stop positions of the three containers 1, that is, first inspection position (A), second inspection position (B), and third inspection position (C) and to the positions of two calibration containers 61 (61A, 61B) outside the three containers 1, that is, first calibration position (D) and second calibration position (E).

As has been discussed, the calibration containers 61 are disposed on both ends of the support pedestal 41, that is, at the front and the rear of the support pedestal 41. The calibration containers 61 are shaped like boxes composed of a translucent material (e.g., an acrylic sheet) and are filled with nitrogen gas as inert gas having a predetermined oxygen concentration. For example, the calibration container 61A has an oxygen concentration of 5% and the calibration container 61B has an oxygen concentration of 10%.

Figure 10:
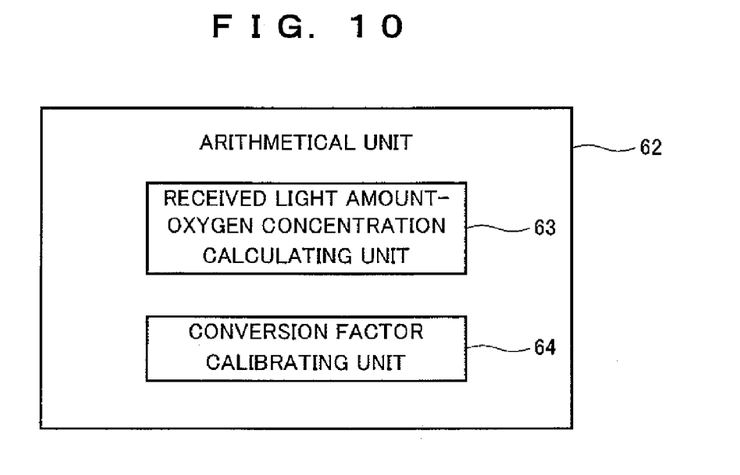
FIG. 10 is a block diagram schematically showing the configuration of an arithmetical unit of the non-destructive inspection device.

As shown in FIG. 10, the non-destructive inspection device 6 includes an arithmetical unit 62. The arithmetical unit 62 includes a received light amount-oxygen concentration calculating unit 63 that receives a detected value from the laser receiving section 48B, that is, an amount of transmitted laser light as an amount of received light, and determines an oxygen concentration; and a conversion factor calibrating unit 64 that receives the detected values of oxygen concentrations in the two calibration containers 61 and calibrates a conversion factor (also called a sensitivity coefficient) R set for the received light amount-oxygen concentration calculating unit 63.

Figure 11:
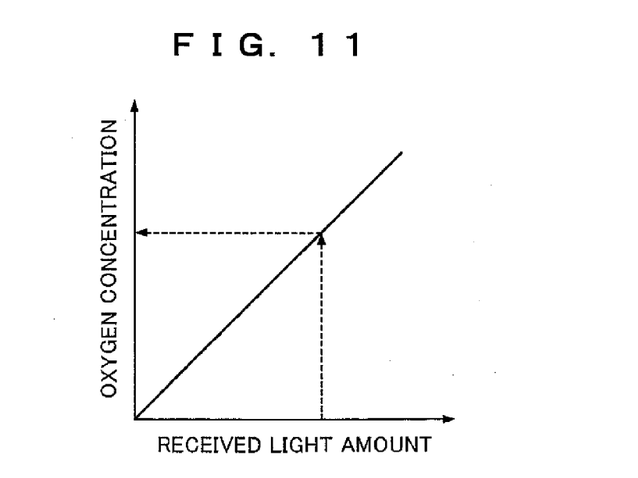
FIG. 11 is a graph showing the relationship between an oxygen concentration and an amount of laser light received for the inspection of the non-destructive inspection device.
Figure 12:
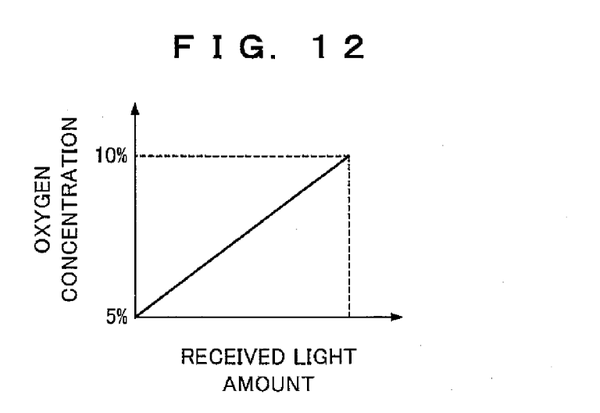
FIG. 12 is a graph showing the relationship between an oxygen concentration and an amount of laser light received for the calibration of the non-destructive inspection device.

For example, as shown in FIG. 11, a graph of the relationship between an amount of received light and an oxygen concentration, that is, the conversion factor R is set for the received light amount-oxygen concentration calculating unit 63. As shown in FIG. 12, for the conversion factor calibrating unit 64, a current graph, that is, a conversion factor R' is determined based on an amount of received light in the inspection of the two calibration containers 61. As a matter of course, this graph is determined by measuring an amount of light received at a concentration of 5% and an amount of light received at a concentration of 10%. Moreover, oxygen concentrations in the two calibration containers 61 can be properly changed according to the measurement range of a measurement target. For example, the oxygen concentrations are 10% and 20%.

The determined graph, that is, the new conversion factor R' is inputted to the received light amount-oxygen concentration calculating unit 63 and is used thereafter. When the conversion factor hardly changes, the current conversion factor R is naturally used.

In this configuration, the containers 1 are moved from the feeding/ejecting machine to the receiving area 5A of the transport path 5 and are sequentially held in groups of three by the container holders 16 provided on the ring plate 15.

In the gas feeding area 5B, nitrogen gas is fed from the inlets 2 into the containers 1. In the subsequent liquid feeding area 5C, a liquid is fed from the inlets 2. After that, the containers 1 are moved to the sealing area 5D to seal the inlets 2 and then the containers 1 are moved to the inspection area 5E to check oxygen concentrations, that is, the quality of the containers 1.

In the inspection area 5E, the three containers 1 are stopped (as a matter of course, the shoulder portions 1a of the containers 1 are pressed inward by the container holders 31 at this point and thus the gas phase portions K substantially have a constant thickness) and then the three containers 1 are sequentially inspected.

In other words, the inspection tools 49 stopped at the first calibration position (D) are moved to the first inspection position (A).

Figure 8:
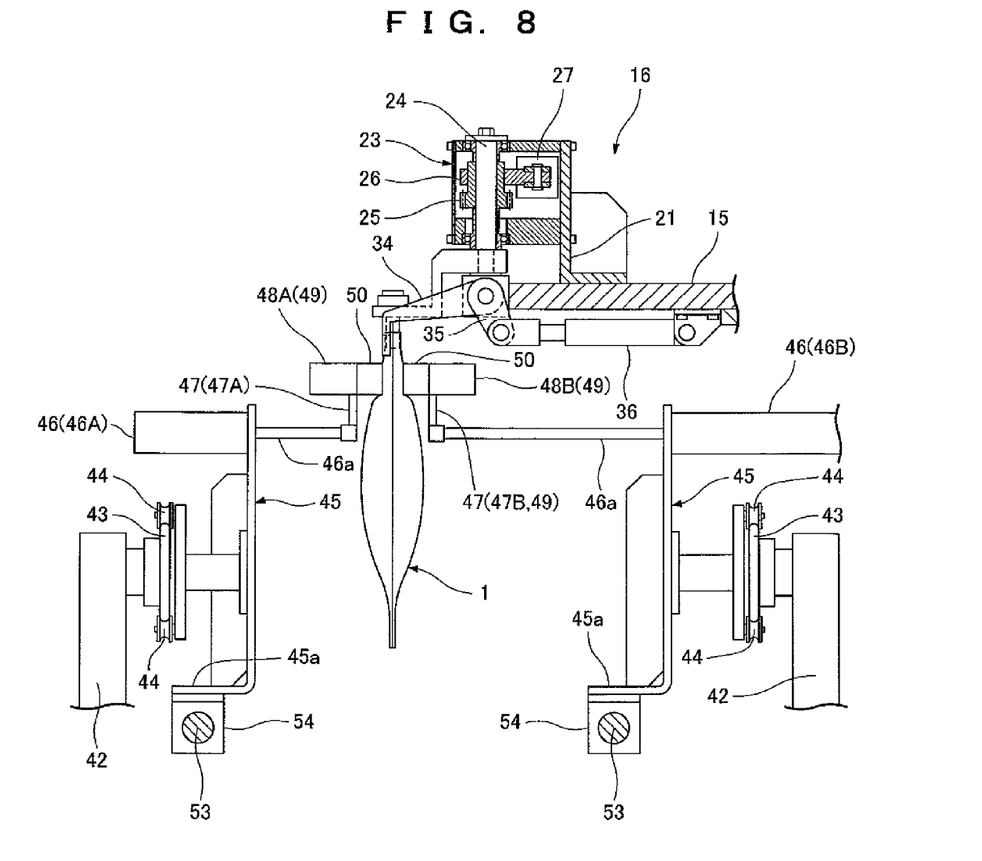
FIG. 8 is a sectional view showing the principle part of the non-destructive inspection device during an inspection.
Figure 9:
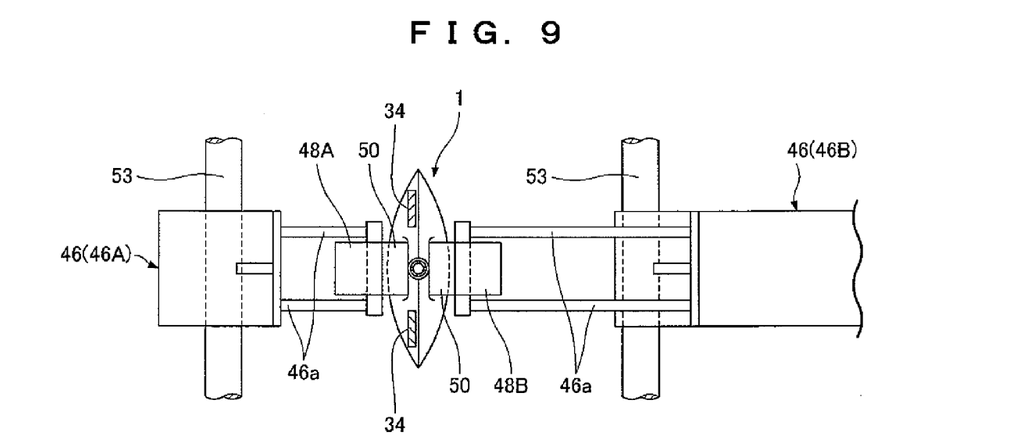
FIG. 9 is a plan view showing the principle part of the non-destructive inspection device during the inspection.

At the first inspection position (A), as shown in FIGS. 8 and 9, the affixing plates 47 are protruded to the container 1 by the movement air cylinders 46. In other words, the right and left gas-filled chambers 50 are brought close to each other to sandwich the center portion of the container 1, that is, the gas phase portion K from both sides with a constant distance, and an air layer is removed between the gas-filled chambers 50 and the gas phase portion K of the container 1.

In this state, a laser beam is emitted from the laser emitting section 48A, passes through the container 1, and is received by the laser receiving section 48B.

The arithmetical unit 62 receives the amount of received light, that is, the amount of the transmitted laser beam detected by the laser receiving section 48B. In the arithmetical unit 62, an oxygen concentration is determined based on the amount of received laser beam (also called an extinction ratio) and then it is decided whether the oxygen concentration is proper or not, in other words, the quality of the container 1 is decided. As a matter of course, a decision unit (not shown) is provided that decides whether an oxygen concentration is proper or not by comparing the oxygen concentration with a set value.

At the completion of the inspection at the first inspection position (A), the laser emitting section 48A and the laser receiving section 48B are moved to the second inspection position (B) by the moving apparatus 51 and the second container 1 is similarly inspected. After that, the laser emitting section 48A and the laser receiving section 48B are moved to the third inspection position (C) by the moving apparatus 51 and the third container 1 is inspected.

When it is decided that an oxygen concentration in the container 1 is not proper, that is, when the oxygen concentration exceeds a permissible value, it is decided that the container 1 is defective. Thus the container 1 is transported to the defective item ejection area 5G and is ejected to the outside without being covered with a protective film.

At the completion of the inspections of the three containers 1, the rotating unit 12 rotates the ring plate 15 to transport the subsequent three containers 1 to the inspection area E and the containers 1 are inspected. In the subsequent inspections, the inspection tools 49 are sequentially moved in the opposite direction from the previous inspection to inspect the three containers 1.

When the inspection tools 49 are moved to one of the calibration positions (D or E), the same inspection as the container 1 is conducted at each position. The calibrating operation is performed beforehand at a set time, for example, every several hours or at the start of an operation on that day.

An inspection result in the calibration is inputted to the conversion factor calibrating unit 64 and calibration is performed on the graph of the relationship between an amount of the received laser beam and an oxygen concentration, that is, the conversion factor R.

As has been discussed, the container holders press the shoulder portion near the gas phase portion of the container, and the inert gas chambers on the ends of the laser emitting section and the laser receiving section are filled with nitrogen gas. In this state, the gas phase portion of the container is pressed to a constant thickness by the ends of the laser emitting section and the laser receiving section from both surfaces, air is removed between the end faces of the laser emitting section and the laser receiving section and the surfaces of the gas phase portion of the bag-shaped container, and a laser beam is emitted to measure an oxygen concentration. Thus even when the container is a soft bag, it is possible to accurately measure the oxygen concentration and decide whether the oxygen concentration is proper or not, that is, the quality of the product. Further, a one hundred percent inspection can be performed. For example, in the related art, in order to accurately measure an oxygen concentration in a soft container such as a bag, it is necessary to collect gas in the container and thus only a sample inspection can be conducted, whereas in the present invention, the foregoing configuration can achieve a one hundred percent inspection.

When an inspection is not conducted, the inspection tools are moved to the calibration position and thus calibration can be performed on the inspection tools, that is, the laser emitting section and the laser receiving section, achieving accurate measurement all the time.

Figure 13:
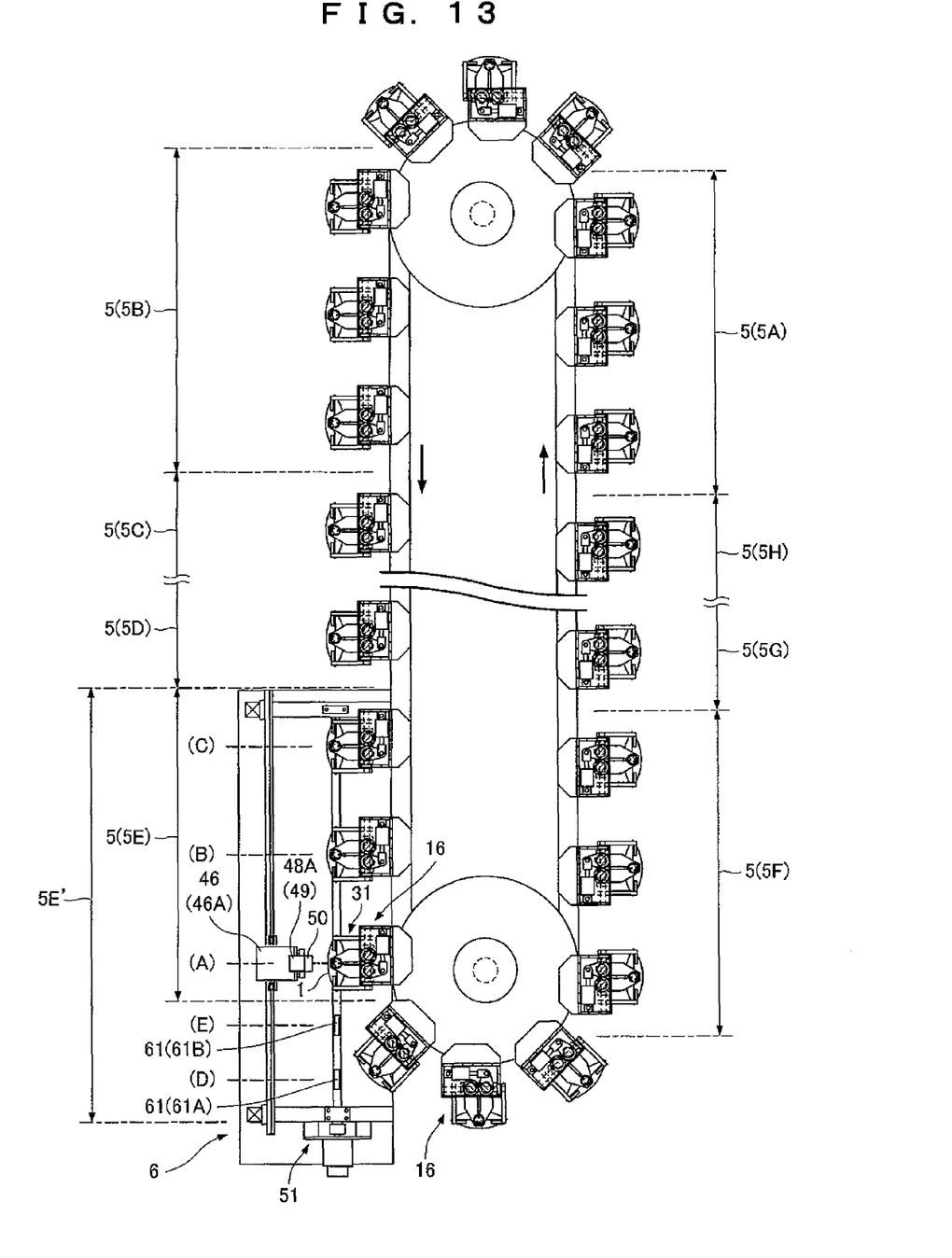
FIG. 13 is a plan view schematically showing the configuration of the principle part of the non-destructive inspection device used for another liquid filler according to the embodiment of the present invention.

In the present embodiment, the transport path 5 of the containers is circular. For example, the transport path 5 may be oval as shown in FIG. 13. Also in this case, the same effect can be achieved as in the present embodiment. The calibration positions (D) and (E) are placed outside the transport path 5 of the containers, e.g., outside the semicircular parts of the transport path 5. In this case, the two calibration positions are placed outside one of the semicircular parts.

Having described the invention, the following is claimed:

1. A non-destructive inspection device for an oxygen concentration in a bag-shaped container, the non-destructive inspection device being provided in a liquid filler for feeding a liquid into the bag-shaped containers held by container holders on a transport unit and transported along a transport path including at least a liquid filling area, a sealing area, and an inspection area, the non-destructive inspection device emitting, in the inspection area of the transport path, a laser beam to a gas phase portion of the bag-shaped container filled with the liquid and measuring an oxygen concentration in the bag-shaped container based on an amount of transmitted light, the non-destructive inspection device comprising:
a pair of right and left moving members provided on right and left of the inspection area of the transport path such that the moving members are moved toward and away from the bag-shaped container by a moving device;
a laser emitting section that is provided on one of the moving members and emits the laser beam for measuring the oxygen concentration; and
a laser receiving section that is provided on the other moving member and receives the laser beam, wherein the non-destructive inspection device further comprises inert gas chambers respectively on end faces of the laser emitting section and the laser receiving section on the moving members, the inert gas chambers being made of a translucent material with a constant length in a depth direction, and in measurement of the oxygen concentration in the inspection area, the pair of right and left moving members are brought close to each other to contact the end faces of the laser emitting section and the laser receiving section with surfaces of the gas phase portion of the bag-shaped container, so that the gas phase portion has a constant thickness and air is removed between the end faces of the laser emitting section and the laser receiving section and the surfaces of the gas phase portion.

2. The non-destructive inspection device for an oxygen concentration in a bag-shaped container according to claim 1, further comprising two calibration containers that are made of a translucent material outside the inspection area and are filled beforehand with inert gas having different oxygen concentrations, wherein the pair of moving members having the laser emitting section and the laser receiving section are movable to calibration positions for measuring the oxygen concentrations in the calibration containers.

3. The non-destructive inspection device for an oxygen concentration in a bag-shaped container according to claim 1, wherein in inspections of the bag-shaped containers, the transport unit is stopped, and the pair of moving members having the laser emitting section and the laser receiving section is movable to the stopped bag-shaped containers.

4. The non-destructive inspection device for an oxygen concentration in a bag-shaped container according to claim 1, wherein the transport path is circular or oval.

* * * * *